United States Patent [19]

Henery et al.

[11] Patent Number: 4,543,437

[45] Date of Patent: Sep. 24, 1985

[54] REFINING OF TERTIARY BUTYLSTYRENE

[75] Inventors: James D. Henery; Stephen C. McHaney; Charles L. Edwards, all of Odessa, Tex.

[73] Assignee: El Paso Products Company, Odessa, Tex.

[21] Appl. No.: 685,929

[22] Filed: Dec. 24, 1984

[51] Int. Cl.$^4$ ............................................. C07C 7/10
[52] U.S. Cl. ..................................... 585/857; 585/865
[58] Field of Search ................ 585/857, 856, 864, 865

[56] References Cited

U.S. PATENT DOCUMENTS

| 3,435,087 | 3/1969 | Broughton | 585/857 |
| 3,544,453 | 12/1970 | Thompson | 585/857 |
| 3,558,480 | 1/1971 | Broughton | 585/865 |
| 3,761,403 | 9/1973 | Plummer | 585/865 |
| 4,385,196 | 5/1983 | Carter | 585/857 |

FOREIGN PATENT DOCUMENTS

| 9135927 | 5/1973 | Japan | 585/857 |
| 0024858 | 2/1979 | Japan | 585/857 |

Primary Examiner—D. E. Gantz
Assistant Examiner—A. Pal
Attorney, Agent, or Firm—Fred S. Valles; Margareta LeMaire

[57] ABSTRACT

Dialkenylbenzene compounds, present in t-butylstyrene in small quantities as impurities are removed by liquid/liquid extraction using aqueous sulfolane as solvent.

5 Claims, No Drawings

REFINING OF TERTIARY BUTYLSTYRENE

BACKGROUND OF THE INVENTION

The invention relates broadly to the manufacture of pure t-butylstyrene and in particular to the refining of t-butylstyrene for removal of dialkenylbenzene impurities.

Tertiary-butylstyrene (tBS) is a compound which is advantageously prepared by catalytic oxidative dehydrogenation (OXD) of t-butylethylbenzene (tBEB). Tertiary-butylstyrene has many uses; e.g., as a chemical intermediate, as a monomer or comonomer in the production of polymeric materials, and the like. Teriary-butylstyrene has often replaced styrene in some applications because desirable physical and chemical product properties result from such a substitution. In addition, there are processes where styrene is not suitable but where tBS functions well.

Because tBS belongs to the same family as styrene, there are similarities in the chemistry of its preparation. One of the common properties is the tendency for the styrenics to polymerize whenever they are activated by chemicals or by heat. Some of the techniques used in purifying styrene can be used to purify tBS. However, because the boiling point of tBS is about 70° C. higher than that of styrene, the tendency for tBS to polymerize is much greater than that of styrene in any of the commercial processes for purifying styrene.

Some of the differences between styrene and tBS derive from the compounds of the dialkenylbenzene family that are present in tBS but not in styrene. These crosslinking compounds can polymerize to give a type of polymer that interferes with the operation of refining equipment. The crosslinked polymer has a tendency to collect in the equipment and to resist attempts to dissolve it.

In addition to some higher boiling hydrocarbon contaminants, there are particularly two dialkenylbenzene compounds which are present in the crude tBS stream obtained from the OXD reactor; i.e., isopropenylstyrene and butenylstyrene.

Careful conventional distillation of the recovered tBS fraction will remove the higher boiling impurities and also most of the butenylstyrene. However, isopropenylstyrene is very difficult to remove by such conventional distillation and will remain with the tBS at a concentration which is above the maximum limit for many applications. For instance, in some polymerization processes the isopropenylstyrene content that can be tolerated is less than about 100 ppm.

In copending application Ser. No. 646,267, filed Aug. 31, 1984, an extractive distillation process, has been disclosed for the removal of dialkenylbenzene contaminants from t-butylstyrene using anhydrous sulfolane as solvent. This process works well; however, the use of reduced pressure and elevated temperature contribute considerably to the equipment, inhibitor, and utilities costs of the overall process.

Trials with anhydrous sulfolane as solvent in liquid/liquid extraction at mild conditions indicated that pure tBS cannot be produced by this technique because tBS and anhydrous sulfolane are completely miscible.

It is, therefore, a principal object of the present invention to provide a refining process utilizing mild operating conditions to obtain a tBS product containing only trace quantities of dialkenylbenzene contaminants.

THE INVENTION

In accordance with the present invention there is provided a process for the removal of dialkenylbenzene contaminants from a t-butylstyrene stream comprising; introducing said stream as feed to a liquid/liquid extraction zone, intimately contacting said feed in said zone with aqueous sulfolane containing from about 5 to about 30 wt. % water, recovering refined t-butylstyrene depleted in dialkenylbenzene contaminants as raffinate, and recovering an extract enriched in dialkenylbenzene contaminants. The preferred water content of the sulfolane solvent is between about 5 and about 15 wt. %.

The feed should preferably contain a polymerization inhibitor effective in supressing polymerization of tBS and aromatic compounds. Suitable inhibitors include tertiary-butyl catechol, 2,4-dinitrophenol and 2,6-dinitro-m-cresol. The concentration of inhibitor in the feed to the column should range between about 25 and about 1,000 ppm by weight.

The operating conditions used in the process are generally mild. Atmospheric pressure and ambient temperatures, from about 20° C. to about 40° C., are usually employed; although it is entirely within the scope of the invention to employ both higher and lower temperatures, if so desired. For best separation results it is preferred that when temperatures in the aforementioned upper range are used in the separation, the water content of the aqueous sulfolane solvent is also adjusted upwards within its disclosed range. The solvent-to-feed weight ratio should be maintained in a range from about 4:1 to about 30:1 and preferably from about 5:1 to about 20:1. Reflux can be provided to the extract end of the extraction zone to increase the recovery of the tBS from the contaminants. The reflux is provided by returning a portion of the extract from which the solvent has been removed. Suitably, the reflux ratio for the extract end is maintained between about 8:1 and about 50:1.

Any efficient liquid/liquid contacting apparatus may be used for the extraction process of this invention. Countercurrent devices such as mixer-settler extractors, spray or packed columns, bubble-cap columns, sieve or perforated-tray columns, and the like can be used.

In the operation of the liquid/liquid extraction column it is possible to obtain a raffinate stream of tBS containing very small quantities of isopropenylstyrene; i.e., below 100 ppm. In addition, other tBS feed contaminants, such as butenylstyrene, have also been reduced to even lower concentrations.

A Small amount of sulfolane is usually present in the raffinate in amounts from about 8 to about 15 wt. %. The sulfolane is easily removed by one or more water washes. The washed tBS can, if desired, be dried before it is sent to final product storage.

The extract product containing the aqueous sulfolane solvent and the extracted impurities is usually recycled to the process. To prevent excessive accumulation of the impurities in the sulfolane, it is preferable that at least a portion of said aqueous sulfolane be treated; e.g., by periodic or continuous distillation. The distilled sulfolane, after adjustment of water content, is then returned to the process.

The following examples illustrate the invention but are not intended to limit its scope.

EXAMPLE 1

A feed containing 98.55 wt. % tBS, 0.0080 wt. % butenylstyrene and 0.4893 wt. % of an impurity which was mostly isopropenylstyrene was subjected to countercurrent liquid/liquid extraction using a York-Scheibel Model XA-1 column extractor containing 11 mixer settler stages. The column was 1" diameter ×48" tall. The mixer sections were 0.5" with a 3" settling zone. The hydrocarbon feed was fed into the bottom of the column at the rate of 4.0 ml/min and sulfolane containing 10 wt. % water was fed into the top of the column at 25.1 ml/min. The mixer stirring rate was 240 rpm. Extract was taken from the bottom of the column at a rate of 27 ml/min and the raffinate was withdrawn from the top at a rate of 3.7 ml/min. Each phase analyzed for tBS and impurities and a selectivity was calculated from the equation:

$$\beta = \frac{\frac{[X]}{[tBS]} \text{Extract}}{\frac{[X]}{[tBS]} \text{Raffinate}}$$

where X is either butenylstyrene or isopropenylstyrene. In this experiment the respective β-values were 1.91 and 4.94. Other pertinent data from the experiment is shown in Table I.

TABLE I

| COMPOSITION OF EXTRACT AND RAFFINATE (Wt. %) | | | | |
|---|---|---|---|---|
| Component | Raffinate | Extract | Raffinate[1] | Extract[1] |
| tBS | 84.9 | 4.91 | 98.66 | 98.36 |
| Butenylstyrene | .004 | .0005 | 0.0047 | 0.0091 |
| Isopropenylstyrene | .146 | .0437 | 0.1725 | 0.8848 |
| Sulfolane | 13.9 | 95 | — | — |

[1]Solvent Free Basis

EXAMPLE 2

The main difference between the condition of this example and that of the preceeding one was that the water concentration of the sulfolane solvent was increased to 20 wt. %. The column rates were as follows: hydrocarbon feed (same as in Example 1) 4 ml/min, solvent feed 27 ml/min, raffinate 4 ml/min, and extract 27 ml/min. The mixer rate was 300 rpm. The results are shown in Table II. The selectivity of butenylstyrene removal was 1.4 and that of isopropenylstyrene removal was 2.46.

TABLE II

| COMPOSITION OF EXTRACT AND RAFFINATE (Wt. %) | | | | |
|---|---|---|---|---|
| Component | Raffinate | Extract | Raffinate[1] | Extract[1] |
| tBS | 88 | 1.96 | 98.51 | 98.29 |
| Butenylstyrene | 0.0060 | 0.0002 | 0.0068 | 0.0095 |
| Isopropenylstyrene | 0.3208 | 0.0176 | 0.3644 | 0.8872 |
| Sulfolane | 10.7 | 98 | — | — |

[1]Solvent Free Basis

EXAMPLE 3

Example 1 was repeated except that the hydrocarbon feed contained 99.39 wt. % tBS and 0.0328 wt. % isopropenylstyrene contaminant resulting in a selectivity of 3.81 for the system to remove the contaminant. The data are listed in Table III.

TABLE III

| COMPOSITION OF EXTRACT AND RAFFINATE (Wt. %) | | | | |
|---|---|---|---|---|
| Component | Raffinate | Extract | Raffinate[1] | Extract[1] |
| tBS | 83.8 | 5.67 | 98.9 | 99.5 |
| Isopropenylstyrene | 0.2795 | 0.0027 | 0.0122 | 0.0468 |
| Sulfolane | 15.3 | 94.3 | — | — |

[1]Solvent Free Basis

All of the Examples 1–3 show that the impurities can be concentrated in the extract phase of the column and that tBS is being separated from the dialkenylbenzene contaminants.

However, if the solvent does not contain any water or if the water concentration is too small, all of the feed components are soluble in the sulfolane and no separation occurs. This was observed in laboratory experiments by contacting tBS containing dialkenylbenzene contaminants with sulfolane containing 0, 1.75 and 2.0 wt. % water.

It is obvious to those skilled in the art that many variations and modifications may be made without departing from the spirit and scope of the invention as herein described and defined in the appended claims.

What is claimed is:

1. A process for the removal of dialkenylbenzene contaminants from a t-butylstyrene stream comprising:
   introducing said stream as feed to a liquid/liquid extraction zone;
   intimately contacting said feed in said zone with aqueous sulfolane solvent containing from about 3 to about 30 wt. % water;
   recovering refined t-butylstyrene depleted in dialkenylbenzene contaminants as raffinate; and recovering an extract enriched in dialkenyl benzene contaminants.

2. The process of claim 1 wherein the water content of the solvent is between about 5 and about 15 wt. %.

3. The process of claim 1 wherein the solvent to feed ratio is maintained in a range from about 4:1 to about 30:1.

4. The process of claim 3 wherein the solvent to feed ratio is between about 5:1 and about 20:4.

5. The process of claim 1 wherein reflux is provided at the extract end of the extraction zone at a ratio of between about 8:1 and about 50:1.

* * * * *